United States Patent [19]

Lang

[11] Patent Number: 5,398,556
[45] Date of Patent: Mar. 21, 1995

[54] DEVICE FOR CHARGING A MEASURING APPARATUS FOR THERMAL ANALYSIS WITH MATERIAL SPECIMENS FILLED INTO CONTAINERS

[75] Inventor: Karl Lang, Jona, Switzerland

[73] Assignee: Mettler-Toledo AG, Greifensee, Switzerland

[21] Appl. No.: 83,986

[22] Filed: Jun. 25, 1993

[30] Foreign Application Priority Data

Aug. 12, 1992 [CH] Switzerland .......... 2521/92

[51] Int. Cl.⁶ ............................................. G01N 25/00
[52] U.S. Cl. .............. 73/863.11; 73/864.81; 374/12; 422/64
[58] Field of Search ........... 73/864.81, 863.11, 863.12; 422/63, 64, 65; 374/12, 45

[56] References Cited

U.S. PATENT DOCUMENTS

| 4,476,733 | 10/1984 | Chlosta et al. ............ | 73/863.11 |
| 4,670,219 | 6/1987 | Nelson et al. ............. | 73/863.11 X |
| 5,064,009 | 11/1991 | Melcher et al. ............ | 177/245 |
| 5,235,862 | 8/1993 | Harada ...................... | 73/863.11 |

FOREIGN PATENT DOCUMENTS

3814959A1  11/1989  Germany .

OTHER PUBLICATIONS

SSC5200 Series–Comprehensive Brochure on Thermal Analysis Systems–Seiko Instruments, Inc. pp. 1–15 published by Jun. 1993.

*Primary Examiner*—Thomas P. Noland
*Attorney, Agent, or Firm*—Friedrich Kueffner

[57] ABSTRACT

A device for charging a measuring apparatus for thermal analysis with material specimens filled into containers includes a vertically displaceable gripping member and a rotatable specimen plate with a plurality of openings arranged in a circle. For transferring a specimen container to the measuring location in the measuring apparatus, the specimen container is moved underneath the gripping member by rotating the specimen plate, the gripping member is lowered and the specimen container is gripped by gripping fingers attached to the gripping member. The container is then raised from the specimen plate by raising the gripping member. Subsequently, the specimen plate is rotated until a recess in the specimen plate is located underneath the gripping member. The measuring location is also located directly underneath the gripping member. By lowering the gripping member through the recess in the specimen plate, the specimen container can now be placed on the measuring location and can be released for carrying out the measurement by spreading apart the gripping fingers.

12 Claims, 3 Drawing Sheets

5,398,556

DEVICE FOR CHARGING A MEASURING APPARATUS FOR THERMAL ANALYSIS WITH MATERIAL SPECIMENS FILLED INTO CONTAINERS

BACKGROUND OF THE INVENTION

1. Field of the Invention

The present invention relates to a device for charging a measuring apparatus for thermal analysis with material specimens or samples filled into containers. The device includes a revolving specimen plate or turntable with cutouts or recesses for receiving the specimen containers and means for gripping, lifting and transferring each container from the specimen plate to a measuring location in the measuring apparatus.

2. Description of the Related Art

Thermal analysis in the narrow sense includes methods of examining materials as a function of temperature, for example, differential thermal analysis (DTA), differential scanning calorimetry (DSC) and thermal gravimetry (TG).

In a broader sense, thermal analysis could also include methods of determining the dry substance or moisture contents of material specimens.

For carrying out measurements on large quantities of specimens of the same type, it is desirable and known in the art to mechanize the manipulation of the specimens partially or entirely by means of charging devices. For example, DE-A1-4023483 discloses an apparatus for dry substance determination in which the specimens are arranged on a turntable within a microwave oven. The weighing dish of the balance is also located within the microwave oven underneath the turntable. The specimens are positioned above openings in the turntable and can be placed individually on the weighing dish by lowering the turntable, so that the weighing dish extends through the opening in the turntable located above the weighing dish. The specimens are picked up again in the reverse sequence.

The known apparatus described above has the disadvantage that all specimens are located within the oven and, therefore, the oven must be opened for charging it with new specimens. In addition, the oven must be very large. A further disadvantage of the known apparatus is to be seen in the fact that the person operating the apparatus does not have an opportunity to observe the apparatus during operation to see whether the specimens are correctly placed on the weighing dish.

DE-A1-3814959 discloses a hygrometer with a specimen changer. The specimens are also placed on a turntable which is provided with openings arranged in a circle. The turntable and the weighing dish of the balance are arranged within the drying chamber and, therefore, are not accessible during measurements.

SUMMARY OF THE INVENTION

Therefore, it is a primary object of the present invention to provide a device for charging measuring apparatus of the above-described type in which the specimens can be arranged outside of the measuring apparatus and are only introduced into the measuring apparatus for carrying out the measurement.

In accordance with the present invention, in a device of the above-described type, the means for gripping, lifting and transferring each container is a gripping member which is mounted vertically displaceably above the specimen plate and above the measuring location.

The various features of novelty which characterize the invention are pointed out with particularity in the claims annexed to and forming a part of the disclosure, For a better understanding of the invention, its operating advantages, and specific objects attained by its use, reference should be had to the drawing and descriptive manner in which there is illustrated and described a preferred embodiment of the invention.

DESCRIPTION OF THE PREFERRED EMBODIMENT

Figure 1:
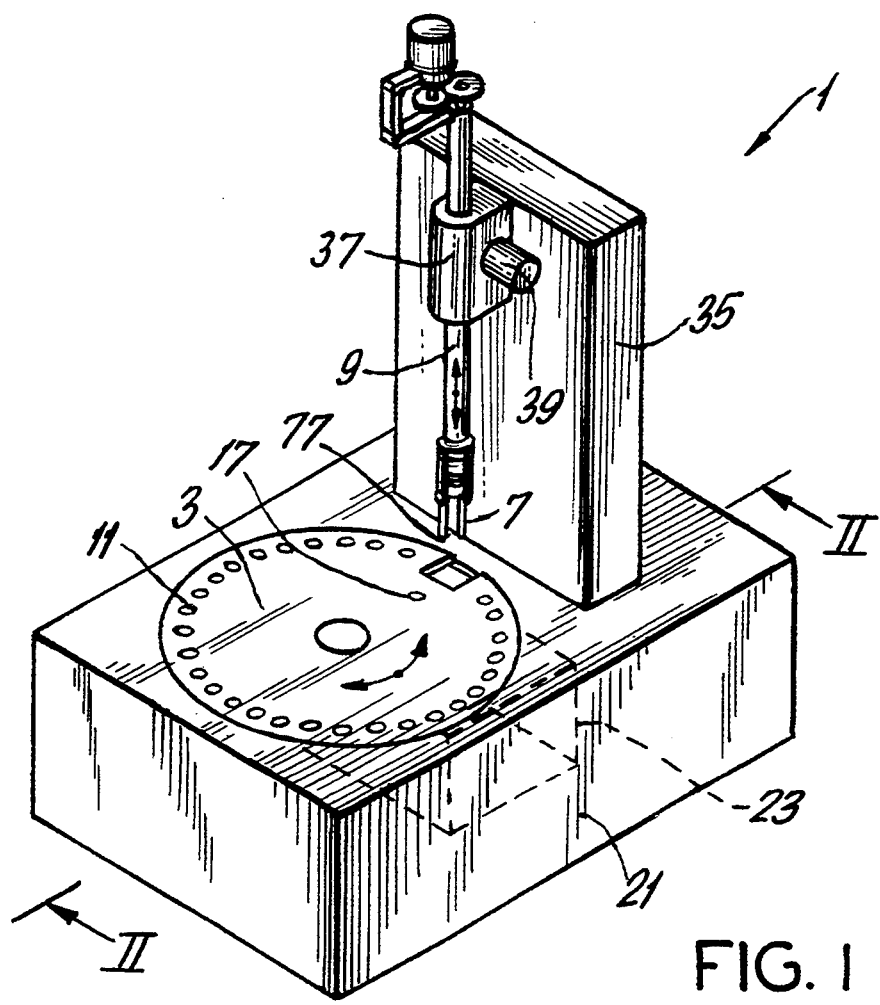
FIG. 1 is a schematic perspective front view of a device for charging containers into a furnace of measuring apparatus for differential scanning calorimetry.
Figure 2:
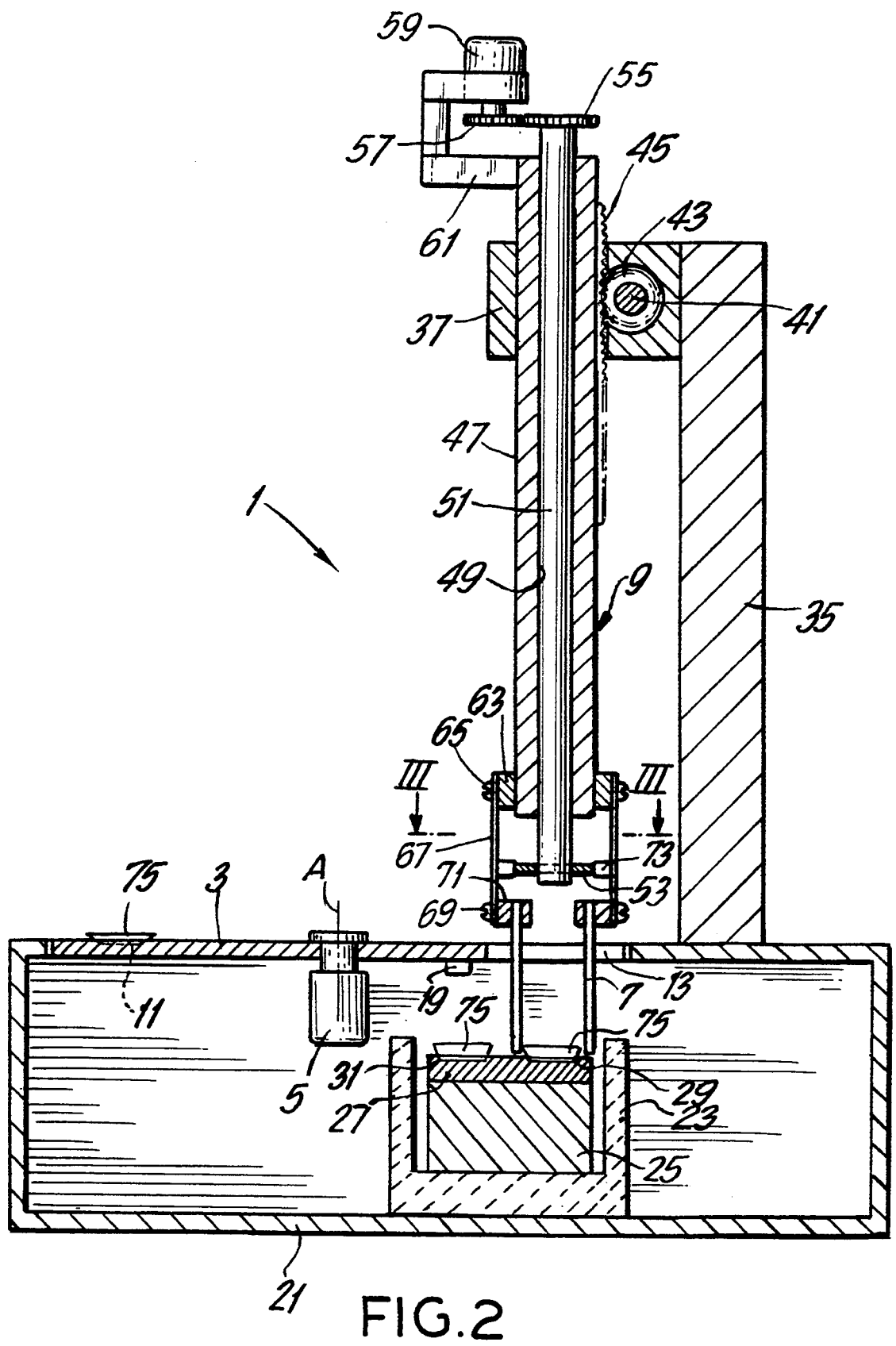
FIG. 2 is a sectional view of the device according to the present invention taken along sectional line II—II of FIG. 1.

In FIGS. 1 and 2 of the drawing, reference numeral 1 denotes a specimen changing device with a disk-shaped specimen plate 3 which is rotatably mounted on an axis A of a drive motor 5. The drive motor 5 preferably is a stepping motor and has the purpose to position the specimen plate 3 under gripping fingers 7 of a vertically displaceably mounted gripping member 9.

Figure 4:
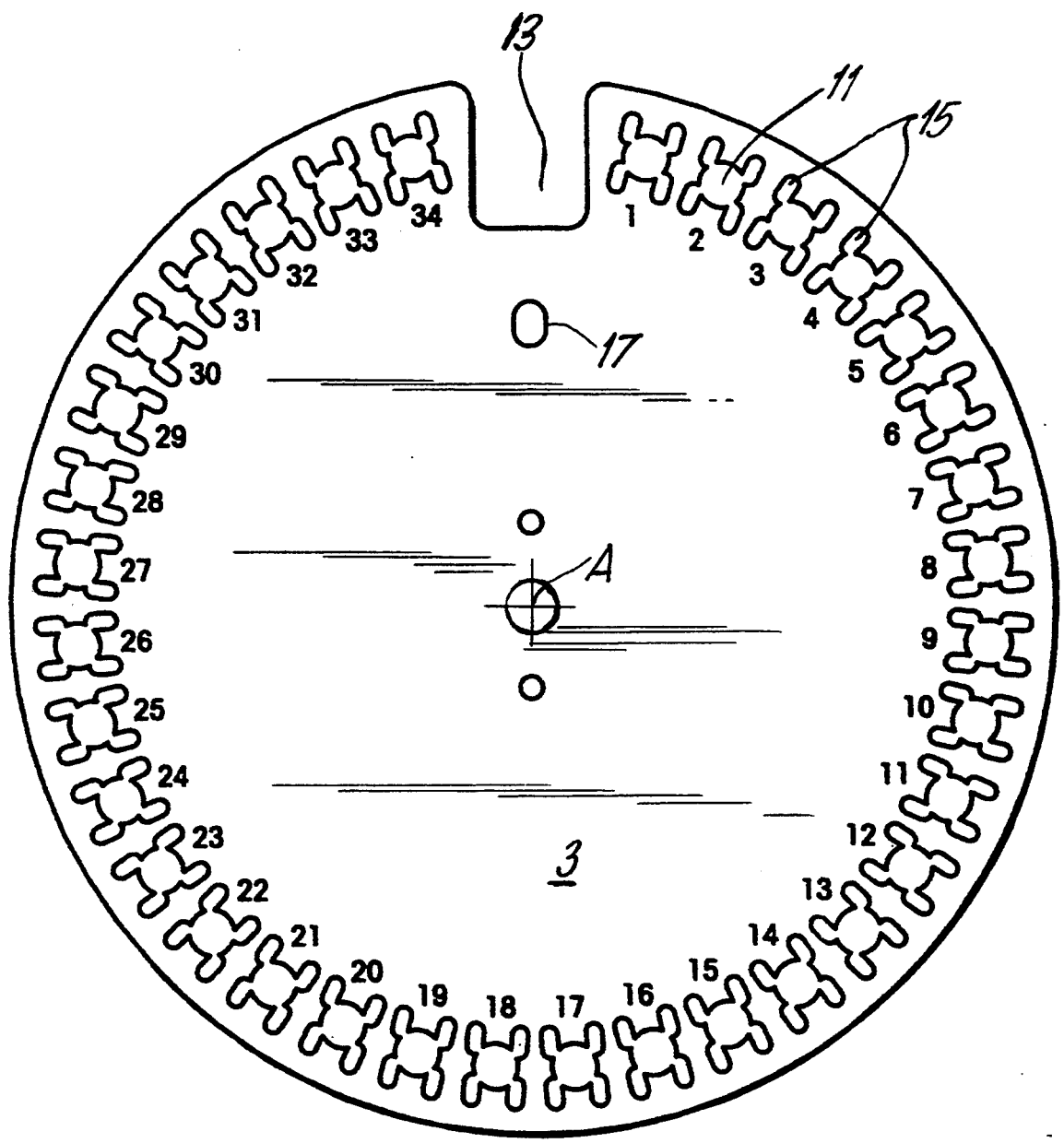
FIG. 4 is a top view of the specimen plate.

FIG. 4 of the drawing shows the specimen plate 3 with a plurality of specimen receiving openings 11. In the illustrated embodiment, 34 specimen receiving openings 11 are provided. The specimen plate 3 has a recess or opening 13 between the first and the thirty-fourth specimen receiving opening. The specimen receiving openings 11 may also be round depressions or bores. The specimen receiving openings 11 additionally have a number of radially outwardly extending indentations or branches 15. The number of indentations or branches 15 corresponds to the number of gripping fingers 7 or to a multiple thereof. The specimen plate 3 additionally has a positioning opening 17 for exactly determining the position of the recess 13. The opening can be scanned by means of a photoelectric cell 19, shown in FIG. 2, or by means of a mechanical scanning device, not shown.

The specimen plate 3 is mounted with its drive motor 5 in a housing 21 which, in the illustrated embodiment, contains a differential scanning calorimetry oven or DSC oven 23. The DSC oven 23 is schematically illustrated, so that the position of the specimen changing device 1 relative to the DSC oven 23, which is important for the sequence of movements, can be seen. In accordance with the DSC procedure, placed on a temperature measuring location 31 is a container 75 which is of the same type as the containers 75 which are transported with the specimens from the specimen plate 3 onto the temperature measuring location 29. The reference container 75 on the temperature measuring location 31 is not exchanged by the specimen changing device 1. Rather, the reference container 75 is exchanged manually by opening the housing 21, for example, by removing the specimen plate 3. In the case of serial measurements, an exchange of the reference container 75 is necessary only relatively infrequently. For the purposes of the present invention, further details of the measuring procedure do not require discussion and, therefore, are not described herein.

The DSC oven 23 contains a heating plate 25 with a carrier plate 27 for the two temperature measuring locations 29 and 31. All other elements of the DSC furnace, such as, the heating coil, the electric connections, and a cover of the oven which may be automatically movable, are not of significance for understanding the present invention and, therefore, are not illustrated or described.

As illustrated in FIGS. 1 and 2 of the drawing, a gripping member support 35 is mounted on the housing 21. A vertical guide bearing member 37 which supports the gripping member 9 is attached to the gripping member support 35 and projects partially over the specimen plate 3. A drive motor 39 is mounted on the vertical guide bearing member 37 attached to the gripping member support 35. A pinion 43 is mounted on a driven shaft 41 of the drive motor 39. The pinion 43 meshes with a rack or toothing 45 provided on the shaft 47 of the gripping member 9. Thus, the drive motor 39 serves to displace the gripping member 9 in vertical direction in the guide bearing the number 37.

The gripping member 9 includes a tubular shaft 47 with a longitudinal bore 49. A shaft 51 is rotatably mounted in the longitudinal bore 49. A cam disk 53 is attached to the lower end of the shaft 51 so as to rotate with the shaft 51. Attached to the upper end of the shaft 51 is a gear wheel 55 which meshes with a pinion 57 mounted on the drive shaft of a motor 59. The motor 59 is fastened to a support 61 on the gripping member 9.

Flat or leaf-type springs 67 are fastened on spacers 63 by means of screws 65 at the lower end of the tubular shaft 47 of the gripping member 9. Sleeves 71 are fastened by means of screws 69 to the lower ends of the flat springs 67. The gripping fingers 7 are supported by the sleeves 71. Cams 73 which are directed toward the axis B of the gripping member 9 are attached to the flat springs 67. As can be seen in FIG. 2 and particularly in FIG. 3, the cams 73 contact the periphery of the cam disk 53.

Figure 5:
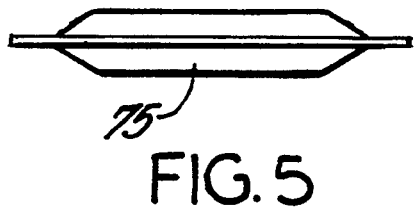
FIG. 5 is a side view of a container closed with a cover.

In the following, charging of a container 75 to the measuring location 29 in the differential scanning calorimetry oven 23 is described. In this example, the container 75 is a very flat, upwardly closed dish as illustrated in FIG. 5.

The number of containers 75 intended for measurement are distributed over the specimen plate 3 in the clover leaf-shaped specimen receiving openings 11. During this step, the specimen plate 3 may be in the initial position as illustrated in FIGS. 1 and 2. In this initial position, the recess 13 in the specimen plate 3 is located axially underneath the gripping member 9. In order to grip the first container 75 which is placed in the opening 11 with the designation number "1" as shown in FIG. 4, the specimen plate 3 is revolved counter-clockwise until the opening 11 with the number "1" is located directly underneath the gripping member 9. In other words, the opening 11 with the number I is moved to the location where the recess 13 was located in the initial position of the specimen plate 3. Subsequently, the gripping fingers 7 on the gripping member 9 are spread apart by rotating the shaft 51 and the cam disk 53 by 45° against the force of the flat springs 67 which support the gripping fingers 7. The rotation of the shaft 51 is effected by the motor 59 at the top of gripping member 9. The gripping member 9 can be vertically lowered by means of the drive motor 39 until the ends 77 of the gripping fingers 7 are located in the radially outwardly extending recesses 15 of the specimen receiving opening 11. As the gripping member 9 is lowered, the ends 77 of the gripping fingers 7 penetrate the plane defined by the surface of the specimen plate 3.

Figure 3:
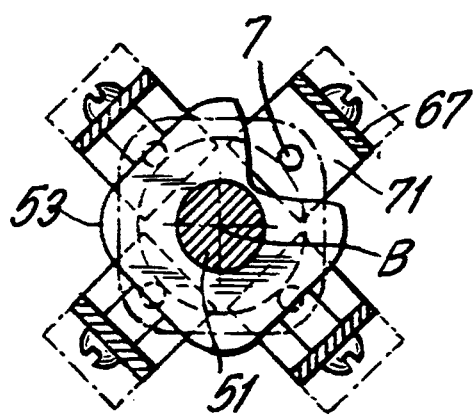
FIG. 3 is a cross-sectional view taken along sectional line III—III of FIG. 2.

When the cam disk 53 is now rotated by 45° by means of the motor 59 into the position illustrated in FIG. 3, the gripping fingers 7 are moved by the flat springs 67 supporting the gripping fingers 7 radially from the outside against the edge of the container 75 to be gripped. The container 75 is securely held by the tension of the four springs 67 which support the gripping fingers 7. It is of no significance in this connection whether the gripping fingers 7 contact the container 75 exactly simultaneously, or whether only three of the four gripping fingers 7 hold the container 75. The container 75 can now be lifted from the specimen plate 3 by raising the gripping member 7 by means of the drive motor 39 whose drive pinion 43 engages the rack 45 on the tubular shaft 47. Subsequently, the specimen plate 3 is returned into the initial position by the motor 5, so that the recess 13 is again located exactly underneath the gripping member 9. The exact positioning of the recess 13 can be monitored by the photoelectric cell 19 with the aid of the positioning opening 17. As soon as this position is reached, the gripping member 9 is lowered through the recess 13 in the specimen plate 3 to such an extent that the container 75 with the specimen is placed on the measuring location 29 within the oven 23. The gripping fingers 7 can be spread apart again by another 45° rotation of the shaft 51 and the container 75 is released for the measurement. In order to be able to close the drying oven 23 from the top by a cover, not shown, the gripping member 9 is moved upwardly into its initial position.

After the measurement has been carried out, the container 75 is removed from the carrier plate 27 in exactly the reverse sequence as carried out previously for charging the measuring apparatus, Of course, instead of four gripping fingers 7, it is also possible to mount only three gripping fingers on the gripping member 9.

It should be understood that the preferred embodiment and examples described are for illustrative purposes only and are not to be construed as limiting the scope of the present invention which is properly delineated only in the appended claims.

I claim:

1. A device for charging a measuring apparatus for thermal analysis with material specimens filled into containers, the measuring apparatus including a measuring location, the device comprising a rotatable specimen plate located outside of the measuring apparatus, the specimen plate having a plurality of receiving means for receiving the specimen containers, and a vertically displaceable gripping means for gripping, lifting and transferring the specimen containers from the specimen plate to the measuring location in the measuring apparatus, the gripping means being mounted above the specimen plate and the measuring location.

2. The device according to claim 1, wherein the receiving means are indentations.

3. The device according to claim 1, wherein the receiving means are openings.

4. The device according to claim 1, further comprising a guide bearing member, the gripping means being vertically displaceably mounted in the guide bearing member, a first drive motor mounted on the guide bearing member, a pinion connected to the first drive motor, and a rack mounted on the gripping member and engaging the pinion.

5. The device according to claim 1, further comprising at least three gripping fingers, spring means connecting the gripping fingers to the gripping member, and spreading means for spreading apart the gripping fingers.

6. The device according to claim 5, further comprising a shaft rotatably mounted in the gripping member, the shaft having an end, the spreading means comprising a cam disk mounted on-the end of the shaft, and a second drive motor for rotating the shaft.

7. The device according to claim 6, wherein the cam disk has a periphery, wherein the spring means are flat springs attached to the gripping fingers, and wherein the flat springs contact the periphery of the cam disk.

8. The device according to claim 5, wherein each receiving means comprises a central portion and a number of extensions extending radially outwardly from the central portion, wherein the number of extensions corresponds at least to the number of gripping fingers.

9. The device according to claim 8, wherein the number of extensions corresponds to a whole number multiple of the number of gripping fingers.

10. The device according to claim 1, wherein the receiving means are clover-leaf shaped.

11. The device according to claim 1, wherein the specimen plate has at least one recess, the recess being shaped such that the gripping member including a specimen container gripped by the gripping member can .be passed through the recess.

12. The device according to claim 11, wherein the specimen plate has a circular portion, the receiving means and the recess being located in the circular portion.

* * * * *